(12) United States Patent
Liu (10) Patent No.: US 10,773,104 B2
(45) Date of Patent: *Sep. 15, 2020

(54) NEUTRON CAPTURE THERAPY SYSTEM

(71) Applicant: NEUBORON MEDTECH LTD., Nanjing, Jiangsu (CN)

(72) Inventor: Yuan-hao Liu, Jiangsu (CN)

(73) Assignee: NEUBORON MEDTECH LTD., Nanjing, Jiangsu Province (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,775

(22) Filed: Apr. 3, 2019

(65) Prior Publication Data

US 2019/0224499 A1 Jul. 25, 2019

Related U.S. Application Data

(63) Continuation of application No. PCT/CN2017/092702, filed on Jul. 13, 2017.

(30) Foreign Application Priority Data

Oct. 31, 2016 (CN) .......................... 2016 1 0930008
Oct. 31, 2016 (CN) ...................... 2016 2 1154870 U (51) Int. Cl.
*A61N 5/10* (2006.01)
*G21G 4/02* (2006.01)
(Continued)

(52) U.S. Cl.
CPC ............. *A61N 5/1077* (2013.01); *A61N 5/10* (2013.01); *A61N 5/1045* (2013.01); *G21G 4/02* (2013.01);
(Continued)

(58) Field of Classification Search
CPC ............... A61N 2005/109; A61N 5/10; A61N 2005/1095; A61N 2005/1094;
(Continued)

(56) References Cited

U.S. PATENT DOCUMENTS 4,252,607 A * 2/1981 Thode ...................... G21B 1/23
376/105
8,541,756 B1 * 9/2013 Treas ...................... G01N 23/09
250/390.01
(Continued)

FOREIGN PATENT DOCUMENTS

CN 102194635 A 9/2011
CN 102473470 A 5/2012
(Continued)

OTHER PUBLICATIONS

International Search Report of PCT/CN2017/092702, dated Oct. 24, 2017.

*Primary Examiner* — David A Vanore
(74) *Attorney, Agent, or Firm* — Locke Lord LLP; Tim Tingkang Xia, Esq.

(57) ABSTRACT

The present disclosure provides a neutron capture therapy system. The neutron capture therapy system includes an accelerator, the accelerator generates a charged particle beam; a neutron generator, the neutron generator generates a neutron beam after being irradiated by the charged particle beam; a beam shaping assembly, the beam shaping assembly includes a moderator and a reflector surrounds around the outer periphery of the moderator, the moderator moderates the neutrons generated by the neutron generator to a preset spectrum, and the reflector leads the deflected neutrons back to increase the neutron intensity within the preset spectrum; and a collimator, the collimator concentrates the neutrons generated by the neutron generator; the spectrum of the
(Continued)

neutron beam is changed by changing the spectrum of the charged particle beam.

18 Claims, 3 Drawing Sheets

(51) Int. Cl.
  *H05H 6/00* (2006.01)
  *G21K 1/06* (2006.01)
  *H05H 3/06* (2006.01)
  *G21K 1/02* (2006.01)
(52) U.S. Cl.
  CPC .............. *G21K 1/02* (2013.01); *G21K 1/062* (2013.01); *H05H 3/06* (2013.01); *H05H 6/00* (2013.01); *A61N 2005/109* (2013.01); *H05H 2277/10* (2013.01)
(58) Field of Classification Search
  CPC ............... A61N 5/1077; A61N 5/1081; A61N 2005/1087; A61N 5/1042; A61N 5/1045; A61N 5/1067; A61N 2005/1098; A61N 5/1049; A61N 5/1064; A61N 5/1071; A61N 2005/005; A61N 2005/1022; A61N 2005/1052; A61N 2005/1055; A61N 2005/1058; A61N 2005/1074
  USPC ............... 250/390.01, 391, 393, 396 R, 398; 376/105, 114, 116, 121, 151
  See application file for complete search history.

(56) References Cited

U.S. PATENT DOCUMENTS

| | | | |
|---|---|---|---|
| 10,082,587 B1* | 9/2018 | Akabori | G01T 7/00 |
| 10,434,333 B2* | 10/2019 | Liu | A61N 5/1077 |
| 10,556,127 B2* | 2/2020 | Liu | A61N 5/10 |
| 2011/0044418 A1* | 2/2011 | Stubbers | H05H 3/06 |
| | | | 376/116 |
| 2013/0092839 A1 | 4/2013 | Kraft et al. | |
| 2015/0216029 A1* | 7/2015 | Tsuchida | B23K 20/021 |
| | | | 376/151 |
| 2016/0193482 A1* | 7/2016 | Fahrig | A61N 5/1067 |
| | | | 600/1 |
| 2018/0160521 A1* | 6/2018 | Hsueh Liu | H05H 6/00 |
| 2019/0030369 A1* | 1/2019 | Mukawa | A61N 5/1031 |
| 2019/0105513 A1* | 4/2019 | Liu | A61N 5/1081 |
| 2019/0224499 A1* | 7/2019 | Liu | A61N 5/10 |
| 2019/0275349 A1* | 9/2019 | Hsiao | G21K 1/10 |
| 2019/0381337 A1* | 12/2019 | Liu | A61K 41/0095 |
| 2019/0388710 A1* | 12/2019 | Hsiao | A61B 6/4258 |

FOREIGN PATENT DOCUMENTS

| | | |
|---|---|---|
| CN | 102971802 A | 3/2013 |
| CN | 104429168 A | 3/2015 |
| CN | 104470193 A | 3/2015 |
| CN | 205073541 U | 3/2016 |
| CN | 205460520 U | 8/2016 |
| EP | 2874473 A1 | 5/2015 |
| JP | 2006047115 A | 2/2006 |

* cited by examiner

NEUTRON CAPTURE THERAPY SYSTEM

RELATED APPLICATION INFORMATION

This application is a continuation of International Application No. PCT/CN2017/092702, filed on Jul. 13, 2017, which claims priority to Chinese Patent Application No. 201610930008.7, filed on Oct. 31, 2016; Chinese Patent Application No. 201621154870.5, filed on Oct. 31, 2016, the disclosures of which are hereby incorporated by reference.

FIELD OF THE DISCLOSURE

The present disclosure relates generally to a radioactive ray irradiation therapy system, and, more particularly, to a neutron capture therapy system.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastomamultiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Figure 1:
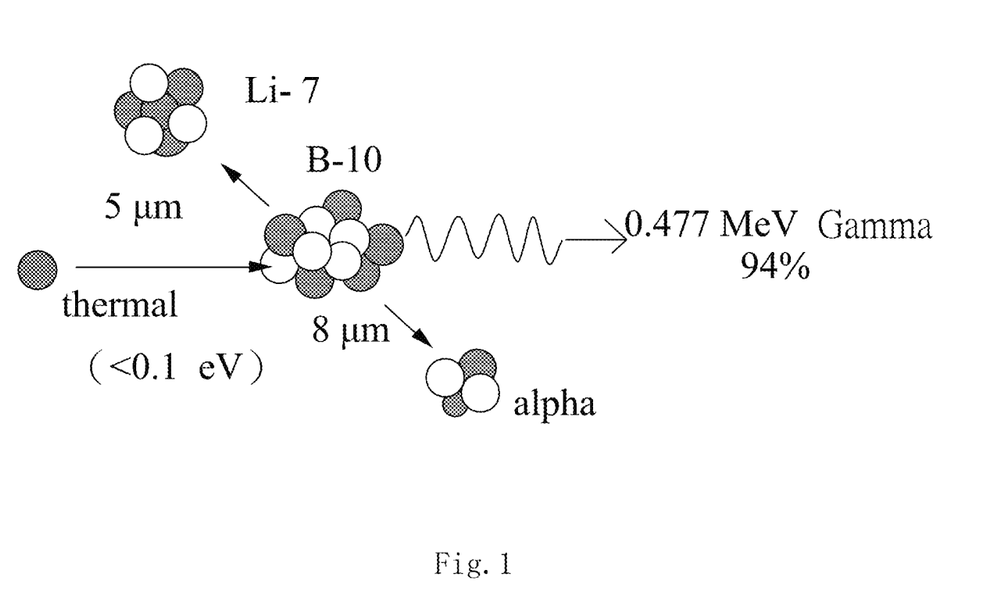
FIG. 1 is a schematic view of a boron neutron capture reaction.

BNCT takes advantage that the boron ($^{10}$B)-containing pharmaceuticals have high neutron capture cross section and produces $^{4}$He and $^{7}$Li heavy charged particles through $^{10}$B(n,α)$^{7}$Li neutron capture and nuclear fission reaction. As illustrated in FIG. 1, a schematic view of boron neutron capture reaction are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^{7}$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

BNCT is also well known for binary cancer therapy, for its effectiveness depending on the concentration of the boronated pharmaceuticals and the number of the thermal neutrons at the tumor site. Thus, besides development of the boronated pharmaceuticals, improvement of quality of the neutron source also plays a significant role in BNCT researches.

Therefore, it is really necessary to provide a new technical solution so as to solve the foregoing problem.

The statements in this section merely provide background information related to the present disclosure and may not constitute prior art.

SUMMARY

In order to obtain neutron beams with various spectrums during neutron capture therapy to meet the requirements for the neutron beam energy spectrum during actual treatments, an aspect of the present disclosure provides a neutron capture therapy system, the neutron capture therapy system includes an accelerator, the accelerator generates a charged particle beam; a neutron generator, the neutron generator generates a neutron beam after being irradiated by charged particle beam; a vacuum tube, the vacuum tube transports the charged particles accelerated by the accelerator to the neutron generator; a beam shaping assembly, the beam shaping assembly includes a moderator and a reflector surrounding the moderator, the moderator moderates the neutrons generated by the neutron generator to a preset spectrum, and the reflector leads the deflected neutrons back to increase the neutron intensity within the preset spectrum; and a collimator, the collimator concentrates the neutrons generated by the neutron generator; the spectrum of the neutron beam is changed by changing the spectrum of the charged particle beam. The spectrum of the neutron beam indirectly changes by changing the spectrum of charged particle beam irradiates to the neutron generator primarily, thereby the depth dose distribution is changed.

Further, in order to achieve different spectrum of charged particle beam, a microwave generator is used to provide different pulses to accelerate the particles source in the accelerator. The neutron capture therapy system includes a microwave generator capable of injecting microwaves into the accelerator, the spectrum of the charged particle beam output by the accelerator changes according to the microwaves injected at different frequencies, when the spectrum of the charged particle beam is at a first value, the charged particles react with the neutron generator and generates a spectrum of neutron beam at a first value, and when the spectrum of the charged particle beam is at a second value, the charged particles react with the neutron generator and generates a spectrum of neutron beam at a second value, wherein the spectrum of the first value of the charged particle beam is lower than that of the second value, and the spectrum of the first value of the neutron beam is lower than that of the second value.

Further, the spectrum of the charged particle beam changes as the changing of electric field intensity of the accelerator (at the accelerator end). The structures before the charged particles and the neutron generator undergo a nuclear reaction are understood to be the accelerator end.

More particularly, an electric field generating device is provided outside the vacuum tube and/or the neutron generator, the electric field generating device is capable of generating an electric field so as to accelerate or decelerate the charged particle beam before the charged particle beam irradiates to the neutron generator. The electric field generating device refers to devices capable of generating an electric field on the outer periphery of the vacuum tube or the neutron generator and capable of accelerating or decelerating the charged particles by the electric field before being irradiated to the neutron generator, for example, an energized electrode.

Further, the neutron capture therapy system further includes a beam energy spectrum adjusting member capable of adjusting the spectrum of the charged particle beam, when the beam energy spectrum adjusting member is located in the vacuum tube and is in front of the neutron generator, the spectrum of the charged particle beam is adjusted after irradiating to the beam energy spectrum adjusting member, and the charged particle beam then irradiates to the neutron generator to generate the neutron beam.

Further, the vacuum tube is provided with an accommodating portion, the beam energy spectrum adjusting member is accommodated in the accommodating portion and is connected with a driving mechanism capable of moving the beam energy spectrum adjusting member, when the driving mechanism controls the beam energy spectrum adjusting member to move to the front of the neutron generator, the spectrum of the charged particles changes after irradiating to the beam energy spectrum adjusting member and then irradiates to the neutron generator; when the driving mechanism controls the beam energy spectrum adjusting member to be accommodated in the accommodating portion but not in front of the neutron generator, the charged particle beam directly irradiates to the neutron generator.

More particularly, the neutron capture therapy system includes a plurality of the beam energy spectrum adjusting members, and different numbers of the beam energy spectrum adjusting members have different spectrum adjustment effects on the charged particle beam, the driving mechanism drives each beam energy spectrum adjusting member to move up or down separately to adjust the spectrum of the charged particle beam. The neutron energy spectrum adjusting member may be made of materials capable of generating neutrons, such as beryllium or lithium.

Each beam energy spectrum adjusting member is made of different materials, and the beam energy spectrum adjusting member made of different materials has different spectrum adjustment effects on the charged particle beam.

Further, the neutron generator is connected to a power supply device and energized by the power supply device, and the beam spectrum of the charged particle beam changes after the charged particles irradiates to the energized neutron generator.

In order to obtain neutron beams with various spectrums during neutron capture therapy to meet the requirements for the neutron beam energy spectrum during actual treatments, another aspect of the present disclosure provides a neutron capture therapy system, the neutron capture therapy system includes an accelerator, the accelerator generates a charged particle beam; a neutron generator, the neutron generator generates a neutron beam after being irradiated by charged particle beam; a vacuum tube, the vacuum tube transports the charged particles accelerated by the accelerator to the neutron generator; a beam shaping assembly, the beam shaping assembly includes a moderator and a reflector surrounding the moderator, the moderator moderates the neutrons generated by the neutron generator to a preset spectrum, and the reflector leads the deflected neutrons back to increase the neutron intensity within the preset spectrum; a collimator, the collimator concentrates the neutrons generated by the neutron generator; and at least a beam energy spectrum adjusting member, before the charged particle beam irradiates to the neutron generator, the charged particle beam irradiates to the beam energy spectrum adjusting member and achieves adjustment of the charged particle beam spectrum.

Further, the beam energy spectrum adjusting member is located in the vacuum tube and is able to move from a first location to a second location, when the beam energy spectrum adjusting member is in the first location, the charged particle beam irradiates to the beam energy spectrum adjusting member before irradiating to the neutron generator; when the beam energy spectrum adjusting member is in the second location, the charged particle beam directly irradiates to the neutron generator.

Further, a plurality of the beam energy spectrum adjusting members are located in the vacuum tube and move from a first location to a second location separately, different members of the beam energy spectrum adjusting members have different effects on the adjustment of the charged particle beam spectrum.

More particularly, the vacuum tube is provided with an accommodating portion located below the neutron generator, the beam energy spectrum adjusting members are accommodated in the accommodating portion, and each beam energy spectrum adjusting member is able to move upward to the first location or downward to the second location separately.

Further, the beam energy spectrum adjusting members are in the same structure but with different thickness, and each beam energy spectrum adjusting member has different effect on the adjustment of the charged particle beam spectrum.

More particularly, the beam energy spectrum adjusting members are made of different materials.

More particularly, at least one of the beam energy spectrum adjusting members is made of materials capable of generating a neutron beam.

In order to obtain neutron beams with various spectrums during neutron capture therapy to meet the requirements for the neutron beam energy spectrum during actual treatments, another aspect of the present disclosure provides a neutron capture therapy system, the neutron capture therapy system includes an accelerator for generating a charged particle beam; a neutron generator for generating a neutron beam after being irradiated by charged particle beam; a vacuum tube for transporting the charged particles accelerated by the accelerator to the neutron generator; a beam shaping assembly including a moderator for moderating the neutrons generated by the neutron generator to a preset spectrum and a reflector surrounding the moderator for leading the deflected neutrons back to increase the neutron intensity within the preset spectrum; a collimator for concentrating the neutrons generated by the neutron generator; and means for changing the spectrum of the charged particle beam, whereby the spectrum of the neutron beam changes, for example, the neutron capture therapy further includes at least a beam energy spectrum adjusting member connected to a driving mechanism for changing the spectrum of the charged particle beam, the beam energy spectrum adjusting member is able to move from a first location to a second location under the controlling of the driving mechanism, when the beam energy spectrum adjusting member is in the first location, the charged particle beam irradiates to the beam energy spectrum adjusting member before irradiating to the neutron generator and achieves adjustment of the charged particle beam, whereby the spectrum of the neutron beam changes; when the beam energy spectrum adjusting member is in the second location, the charged particle beam directly irradiates to the neutron generator.

Further, a plurality of the beam energy spectrum adjusting members are located in the vacuum tube, and move from the first location to the second location separately, different members of the beam energy spectrum adjusting members have different effects on the adjustment of the charged particle beam spectrum.

Compared to the prior art, the neutron capture therapy system of the present disclosure indirectly changes the spectrum of the neutron beam by adjusting the spectrum of the charged particle beam to meet different requirements for the spectrum of the neutron beam under different treatment conditions, and has a simple structure and is easy to implement.

Further areas of applicability will become apparent from the description provided herein. It should be understood that the description and specific examples are intended for purposes of illustration only and are not intended to limit the scope of the present disclosure.

The above described drawing figures illustrate aspects of the disclosure in at least one of its exemplary embodiments, which are further defined in detail in the following description. Features, elements, and aspects of the disclosure that are referenced by the same numerals in different figures represent the same, equivalent, or similar features, elements, or aspects, in accordance with one or more embodiments.

DETAILED DESCRIPTION

The following description of the preferred embodiments is merely exemplary in nature and is in no way intended to limit the invention, its application, or uses.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n)$^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux >1×10$^9$ n/cm$^2$s
Fast neutron contamination <2×10$^{-13}$ Gy-cm$^2$/n
Photon contamination <2×10$^{-13}$ Gy-cm$^2$/n
Thermal to epithermal neutron flux ratio <0.05
Epithermal neutron current to flux ratio >0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than 10$^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than 2*10$^{-13}$Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is called as advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time$\Leftarrow$30 min (proton current for accelerator is 10 mA)
2. 30.0RBE-Gy treatable depth$\geq$=7 cm
3. The maximum tumor dose$\geq$=60.0RBE-Gy
4. The maximum dose of normal brain tissue$\Leftarrow$12.5RBE-Gy
5. The maximum skin dose$\Leftarrow$11.0RBE-Gy Note: RBE stands for relative biological effectiveness. Since photons and neutrons express different biological effectiveness, the dose above should be multiplied with RBE of different tissues to obtain equivalent dose.

In actual neutron capture therapy process, different patients and tumors often require different energies of neutrons, and how to get an appropriate spectrum of the neutron beam for treatment according to the specific situation is to be solved. Before the charged particle beam irradiates to the neutron generator, change its spectrum, so as to provide multiple spectrums of neutron beam. Since the spectrum of the charged particle beam is changed and the neutron beam is generated by the irradiation of the charged particle beam to neutron generator, the spectrum changing of the charged particle beam directly affects the spectrum of the neutron beam. The spectrum of the neutron beam is changed by changing the spectrum of the charged particle beam according to the present disclosure which includes but not limits to boron neutron capture therapy, and the neutron capture therapy system of the present disclosure is specifically described below.

Figure 2:
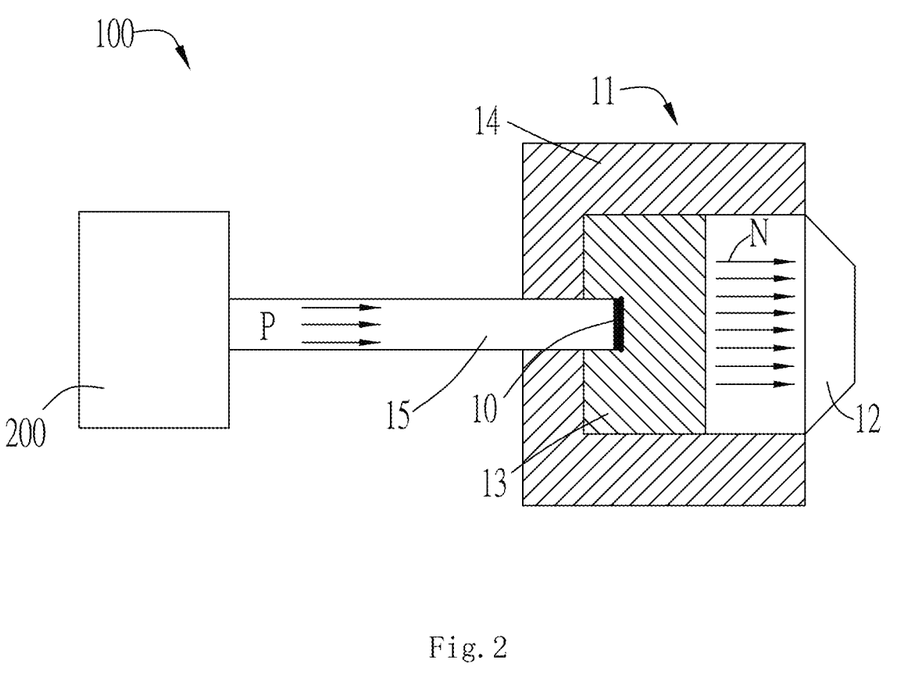
FIG. 2 is a schematic view of a neutron capture therapy system of the present disclosure.

As shown in FIG. 2, the present disclosure provides a neutron capture therapy system 100. The neutron capture therapy system 100 includes an accelerator 200 for generating a charged particle beam P, a neutron generator 10 for generating a neutron beam after being irradiated by the charged particle beam P, a beam shaping assembly 11, and a collimator 12. The beam shaping assembly 11 includes a moderator 13 and a reflector 14 surrounding the moderator 13. The neutron generator 10 generates a neutron beam N after being irradiated by the charged particle beam P, the moderator 13 decelerates the neutron beam N generated by the neutron generator 10 to a preset spectrum, and the reflector 14 leads the deflected neutrons back to increase the neutron intensity within a preset spectrum, and the collimator 12 concentrates the neutrons generated by the neutron generator for irradiation. The spectrum of the charged particle beam can be varied, the neutron capture therapy system 100 indirectly changes the spectrum of the neutron beam generated by the neutron generator by changing the spectrum of the charged particle beam. Since the neutron beam N is generated by irradiating the neutron generator 10 with the charged particle beam P, the spectrum changing of the charged particle beam P affects the spectrum of the neutron beam N. That is, the present disclosure indirectly changes the spectrum of the neutron beam N by changing the spectrum of the charged particle beam P so as to provide a better neutron depth dose distribution.

Figure 3:
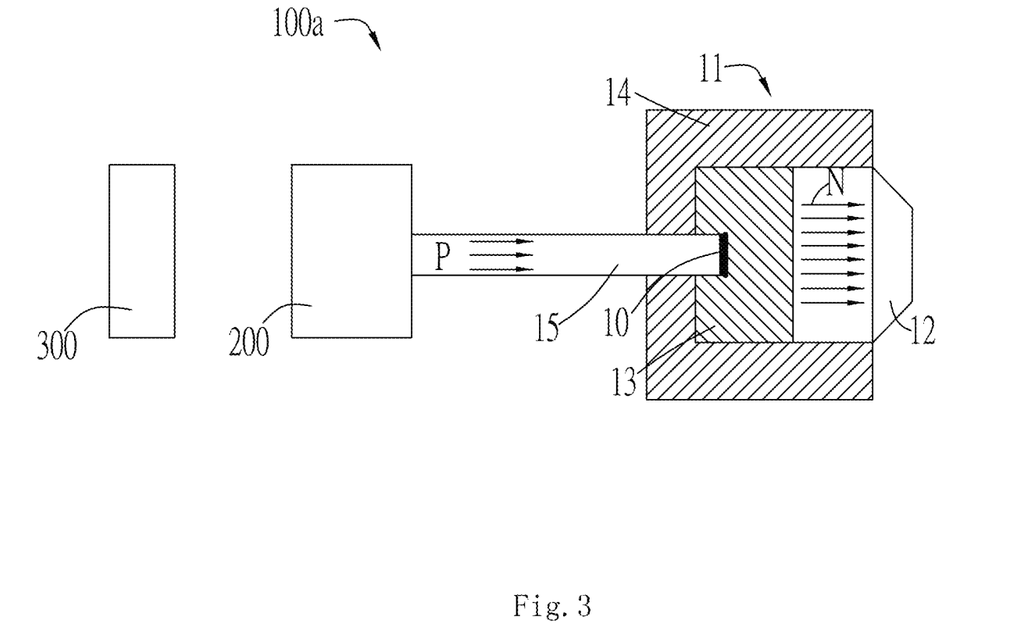
FIG. 3 is a schematic view of a neutron capture therapy system provided with a microwave generator.

As a first embodiment, as shown in FIG. 3, the neutron capture therapy system 100a further includes a microwave generator 300 disposed at accelerator end. Accordingly, the similar features will be labeled with the same numerals, but with an "a" appended thereto. The microwave generator 300 is capable of generating microwaves of different frequencies, and the accelerator 200 accelerates the particle source in the accelerator according to different frequencies of the injected microwaves to change the spectrum of the charged particle beam output by the accelerator. The higher the frequency of the microwave injected into the accelerator 200 is, the faster the accelerator 200 accelerates the particle source, and the higher the spectrum of the charged particle beam P is, the higher the spectrum of the neutron beam N generated by the neutron generator 10 after being irradiated by the charged particle beam P is; the lower the frequency of the microwave injected into the accelerator 200 is, the slower the accelerator 200 accelerates the particle source, and the lower the spectrum of the charged particle beam P is, the lower the spectrum of the neutron beam N generated by the neutron generator 10 after being irradiated by the charged particle beam P is. When the spectrum of the charged particle beam is low (which is named the first value), the spectrum of the neutron beam generated by the reaction of the charged particle with the neutron generator is low (the spectrum value of the first neutron beam); when the spectrum of the charged particle beam is high (which is named the second value), the spectrum of the neutron beam generated by the reaction of the charged particle with the neutron generator is high (the spectrum value of the second neutron beam), wherein the first value is lower than the second value, the spectrum value of the first neutron beam is lower than the spectrum value of the second neutron beam.

Figure 4:
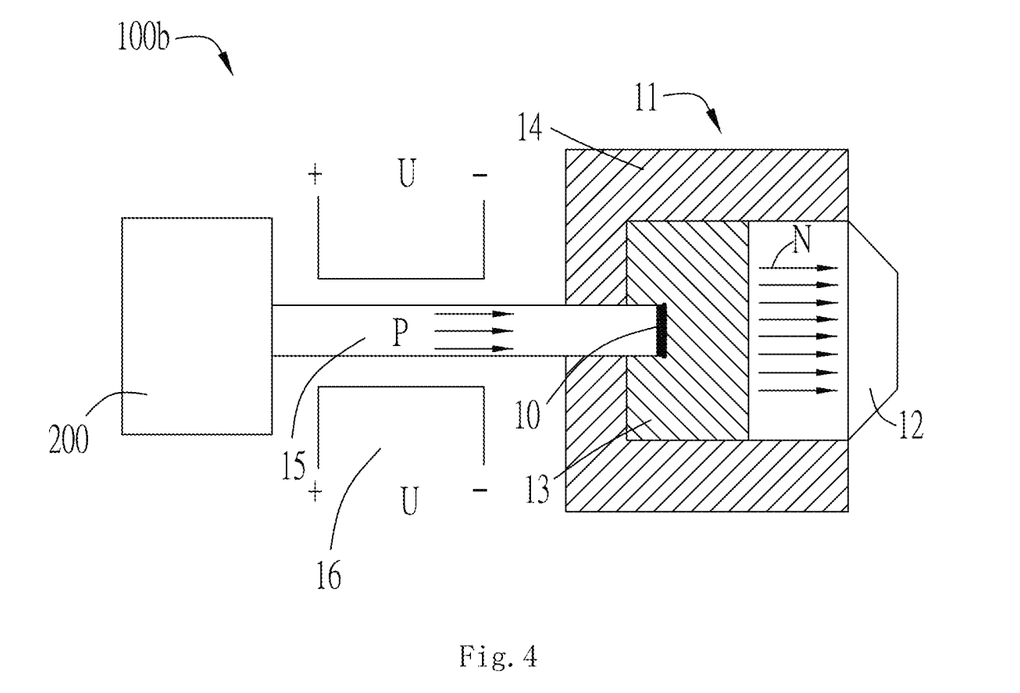
FIG. 4 is a schematic view of a neutron capture therapy system provided with an electric field generating device.

As shown in FIG. 4, as a second embodiment of the neutron capture therapy system 100b, the spectrum of the charged particle beam P is changed by changing the electric field intensity at the accelerator end. Accordingly, the similar features will be labeled with the same numerals, but with a "b" appended thereto. Since the electric field intensity at the accelerator end greatly affects the acceleration speed of the charged particle beam P, and the acceleration speed of the charged particle beam P directly affects the spectrum of the charged particle beam P, the spectrum of the neutron beam N generated by the charged particle beam P irradiates to the neutron generator 10 is affected.

As a specific embodiment for changing the electric field intensity at the accelerator end, the present disclosure provides an electric field generating device 16 outside the vacuum tube 15 or outside the neutron generator 10 to generate an electric field capable of accelerating or decelerating the charged particle beam P before irradiating to the neutron generator 10. Preferably, the electric field generating device 16 refers to an energized electrode. The electric field intensity difference is adjusted by controlling the voltage difference at the energized electrode to accelerate or decelerate the charged particle beam P, and the details will not be described herein.

Actually, the purpose of providing such an electric field generating device 16 outside the vacuum tube 15 or outside the neutron generator 10 is to provide a second adjustment of the spectrum of the charged particle beam P accelerated by the accelerator 200, so as to obtain a neutron beam N with a spectrum level that is required in accordance with the neutron capture therapy when the charged particle beam P irradiates to the neutron generator 10. That is, the spectrum of the charged particle beam P is changed by changing the electric field at the accelerator end so as to indirectly change the spectrum of the neutron beam N. Certainly, such an electric field generating device 16 may also be disposed outside the vacuum tube 15 and outside the neutron generator 10 respectively to adjust the spectrum of the charged particle beam P several times, thereby making it easier to achieve the spectrum adjustment, and finally obtaining the neutron beam N with a spectrum level required for the treatment.

Figure 5:
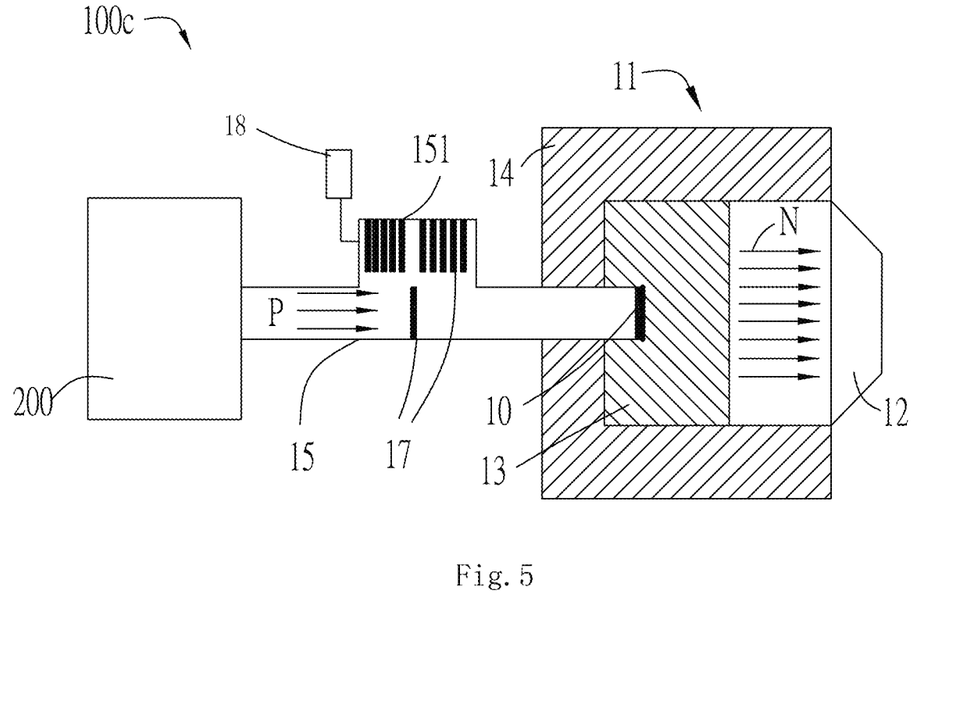
FIG. 5 is a schematic view of a neutron capture therapy system provided with beam energy spectrum adjusting members.

FIG. 5 is a third embodiment of the present disclosure of the neutron capture therapy system 100c for changing the spectrum of the charged particle beam P. Accordingly, the similar features will be labeled with the same numerals, but with a "c" appended thereto. In the present embodiment, a beam energy spectrum adjusting member 17 is located in the vacuum tube 15 and in front of the neutron generator 10, and the charged particle beam P irradiates to the beam energy spectrum adjusting member 17 to perform spectrum adjustment, and then irradiates to the neutron generator 10 to generate a neutron beam N, and finally achieves spectrum adjustment of the neutron beam N.

The beam energy spectrum adjusting member 17 is disposed in the vacuum tube 15 and located below the neutron generator 10. The vacuum tube 15 is provided with an accommodating portion 151 under the neutron generator 10, and the beam energy spectrum adjusting member 17 is accommodated in the accommodating portion 151. Since different numbers of beam energy spectrum adjusting member 17 have different effects on the adjustment of the spectrum of the charged particle beam P, a plurality of beam energy spectrum adjusting members 17 are disposed in the vacuum tube 15, and each beam energy spectrum adjusting member 17 is respectively connected to a driving mechanism 18, and the driving mechanism 18 controls each of the beam energy spectrum adjusting member 17 to move upward or downward respectively, that is, the driving mechanism 18 can simultaneously move one or more of the beam energy spectrum adjusting member 17 upward or downward. During actual neutron capture therapy, the driving mechanism 18 is operated in accordance with the spectrum requirements of the neutron beam N, and the motion of each beam energy spectrum adjusting member 17 is controlled by the driving mechanism 18. When the driving mechanism 18 controls the beam energy spectrum adjusting member 17 to move upward, the beam energy spectrum adjusting member 17 moves in front of the neutron generator 10, and the charged particle beam P irradiates to the beam energy spectrum adjusting member 17 to perform spectrum adjustment, and then the charged particle beam P irradiates to the neutron generator 10; when the driving mechanism 18 controls the beam energy spectrum adjusting member 17 to move downward, the beam energy spectrum adjusting member 17 is accommodated in the accommodating portion 151, and the charged particle beam P directly irradiates to the neutron generator 10. The spectrum of the charged particle beam P is adjusted by the beam energy spectrum adjusting member 17, thereby indirectly adjusts the spectrum of the neutron beam N. Furthermore, the beam energy spectrum adjusting member may be disposed at other positions in the vacuum tube besides the position below the neutron generator, as long as it can be located in or not in front of the neutron generator when the spectrum of the charged particle beam needs or does not need to be adjusted.

In order to facilitate the manufacture and installation of the beam energy spectrum adjusting member 17, each beam energy spectrum adjusting member 17 is designed to have the same structure and each beam energy spectrum adjusting member 17 is sequentially arranged in the accommodating portion 151. The cross sections of the beam energy spectrum adjusting member 17 and the neutron generator 10 perpendicular to the irradiation direction of the charged particle beam P are circular, and the radius of the beam energy spectrum adjusting member 17 is smaller than that of the neutron generator 10. In order to alleviate the heat of the beam energy spectrum adjusting member 17 after being irradiated by the charged particle beam P, a cooling device (not shown) is provided on the outer periphery of the beam energy spectrum adjusting member 17. The arrangement of the cooling device of the beam energy spectrum adjusting member 17 can refer to the cooling method of the neutron generator 10 in the prior art, which will not be specifically described herein. When the charged particle beam P irradiates to the beam energy spectrum adjusting member 17, the beam energy spectrum adjusting member 17 adjusts the spectrum of the charged particle beam P, and the cooling device cools the beam energy spectrum adjusting member 17.

The thickness of each of the beam energy spectrum adjusting members 17 may be the same or different. In addition, the materials of the beam energy spectrum adjusting members 17 may be the same or different. When all the beam energy spectrum adjusting members 17 are made of the same materials, different requirements for the neutron beam N spectrum during neutron capture therapy can be achieved by controlling different numbers of the beam energy spectrum adjusting members 17 to move upward to be in front of the neutron generator 10. When the beam energy spectrum adjusting member 17 is made of different materials, different requirements for the neutron beam N spectrum during neutron capture therapy can be achieved by controlling different numbers of beam energy spectrum adjusting members 17 to move upward, or by the controlling one or several of the beam energy spectrum adjusting members 17 made of different materials to move upward. Alternatively, the beam energy spectrum adjusting member 17 may be made of materials capable of generating a neutron beam N, such as lithium or beryllium. It should be noted that when the beam energy spectrum adjusting member 17 is made of a material capable of generating the neutron beam N, the beam energy spectrum adjusting member 17 should be placed as close as possible to the neutron generator 10, so that both the neutron beam generated by the irradiation of the charged particle beam P to the beam energy spectrum adjusting member 17 and the neutron beam generated by the irradiation of the charged particle beam P to the neutron generator are effectively utilized. Certainly, even the materials of the beam energy spectrum adjusting member 17 can not generate a neutron beam, it also can be used as long as the beam energy spectrum adjusting member 17 is disposed in the vacuum tube 15 and is able to move upward under the control of the driving mechanism 18 to be in front of the neutron generator 10, and realize the spectrum adjustment on the charged particle beam P irradiates to the neutron generator 10.

Figure 6:
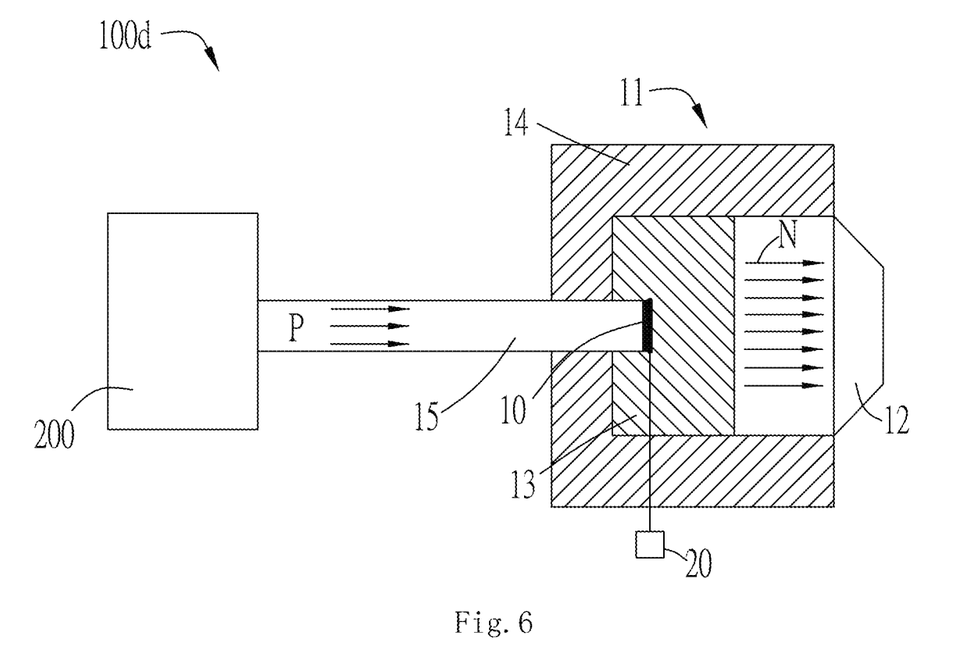
FIG. 6 is a schematic view showing energization of a plating layer of a neutron generator.

Referring to FIG. 6, as a fourth embodiment, the neutron generator 10 of the neutron capture therapy system 100d is connected to a power supply device 20. Accordingly, the similar features will be labeled with the same numerals, but with a "d" appended thereto. The neutron generator 10 is energized by the power supply device 20 to generate an electric field inside the neutron generator, and the beam spectrum of the charged particle beam P changes after the charged particle beam P irradiates to the neutron generator 10 being energized.

Certainly, in order to obtain a neutron beam N with better quality, it is also implementable to provide a microwave generator, an electric field generating device, a beam energy spectrum adjusting member, and a neutron generator connected to a power supply device simultaneously, so as to realize multiple spectrum adjustments on the charged particle beam P during the neutron capture therapy, and make it easier to obtain the neutron beam of the required spectrum level, which will not be specifically described herein.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A neutron capture therapy system comprising:
    an accelerator, wherein the accelerator generates a charged particle beam;
    a neutron generator, wherein the neutron generator generates a neutron beam after being irradiated by the charged particle beam;
    a vacuum tube, wherein the vacuum tube transports the charged particles accelerated by the accelerator to the neutron generator;
    a beam shaping assembly, wherein the beam shaping assembly comprises a moderator and a reflector surrounding the moderator, the moderator moderates the neutrons generated by the neutron generator to a preset spectrum, and the reflector leads the deflected neutrons back to increase the neutron intensity within the preset spectrum; and
    a collimator, wherein the collimator concentrates the neutrons generated by the neutron generator,
    wherein the spectrum of the neutron beam is changed by changing the spectrum of the charged particle beam.

2. The neutron capture therapy system according to claim 1, wherein the neutron capture therapy system further comprises a microwave generator capable of injecting microwaves into the accelerator, the spectrum of the charged particle beam output by the accelerator changes according to the injected microwaves at different frequencies, when the spectrum of the charged particle beam is at a first value, the charged particle beam reacts with the neutron generator and generates a spectrum of neutron beam at a first value, and when the spectrum of the charged particle beam is at a second value, the charged particle beam reacts with the neutron generator and generates a spectrum of neutron beam at a second value, wherein the spectrum of the first value of the charged particle beam is lower than that of the second value, and the spectrum of the first value of the neutron beam is lower than that of the second value, and wherein the neutron capture therapy system indirectly changes the spectrum of the neutron beam by changing the beam energy spectrum of the charged particle beam, and then changes the neutron depth dose distribution.

3. The neutron capture therapy system according to claim 1, wherein the spectrum of the charged particle beam changes as the changing of electric field intensity of the accelerator, an electric field generating device is provided outside the vacuum tube and/or the neutron generator, the electric field generating device is capable of generating an electric field and so as to accelerate or decelerate the charged particle beam before the charged particle beam irradiates to the neutron generator.

4. The neutron capture therapy system according to claim 1, wherein the neutron capture therapy system further comprises a beam energy spectrum adjusting member capable of adjusting the spectrum of the charged particle beam, when the beam energy spectrum adjusting member is located in the vacuum tube and is in front of the neutron generator, the spectrum of the charged particle beam is adjusted after irradiating to the beam energy spectrum adjusting member, and then the charged particle beam irradiates to the neutron generator to generate the neutron beam.

5. The neutron capture therapy system according to claim 4, wherein the vacuum tube is provided with an accommodating portion, the beam energy spectrum adjusting member is accommodated in the accommodating portion and is connected with a driving mechanism capable of moving the beam energy spectrum adjusting member, when the driving mechanism controls the beam energy spectrum adjusting member to move to the front of the neutron generator, the spectrum of the charged particle beam changes after irradiating to the beam energy spectrum adjusting member and then irradiates to the neutron generator; when the driving mechanism controls the beam energy spectrum adjusting member to be accommodated in the accommodating portion but not in front of the neutron generator, the charged particle beam directly irradiates to the neutron generator.

6. The neutron capture therapy system according to claim 5, wherein the neutron capture therapy system comprises a plurality of beam energy spectrum adjusting members, and the driving mechanism drives each beam energy spectrum adjusting member to move separately to adjust the spectrum of the charged particle beam.

7. The neutron capture therapy system according to claim 5, wherein the beam energy spectrum adjusting members are made of different materials.

8. The neutron capture therapy system according to claim 1, wherein the neutron generator is connected to a power supply device and energized by the power supply device, and the beam spectrum of the charged particle beam changes after the charged particle beam irradiates to the energized neutron generator.

9. A neutron capture therapy system comprising:
an accelerator, wherein the accelerator generates a charged particle beam;
a neutron generator, wherein the neutron generator generates a neutron beam after being irradiated by the charged particle beam;
a vacuum tube, wherein the vacuum tube transports the charged particles accelerated by the accelerator to the neutron generator;
a beam shaping assembly, wherein the beam shaping assembly comprises a moderator and a reflector surrounding the moderator, the moderator moderates the neutrons generated by the neutron generator to a preset spectrum, and the reflector leads the deflected neutrons back to increase the neutron intensity within the preset spectrum;
a collimator, wherein the collimator concentrates the neutrons generated by the neutron generator; and
at least a beam energy spectrum adjusting member, wherein before the charged particle beam irradiates to the neutron generator, the charged particle beam irradiates to the beam energy spectrum adjusting member and achieves adjustment of the charged particle beam spectrum.

10. The neutron capture therapy system according to claim 9, wherein the beam energy spectrum adjusting member is located in the vacuum tube and is able to move from a first location to a second location, when the beam energy spectrum adjusting member is in the first location, the charged particle beam irradiates to the beam energy spectrum adjusting member before irradiating to the neutron generator; when the beam energy spectrum adjusting member is in the second location, the charged particle beam directly irradiates to the neutron generator.

11. The neutron capture therapy system according to claim 10, wherein a plurality of beam energy spectrum adjusting members are located in the vacuum tube and move from a first location to a second location separately.

12. The neutron capture therapy system according to claim 11, wherein the vacuum tube is provided with an accommodating portion located below the neutron generator, the beam energy spectrum adjusting members are accommodated in the accommodating portion, and each beam energy spectrum adjusting member is able to move upward to the first location or downward to the second location separately.

13. The neutron capture therapy system according to claim 11, wherein the beam energy spectrum adjusting members are in the same structure but with different thicknesses.

14. The neutron capture therapy system according to claim 11, wherein the beam energy spectrum adjusting members are made of different materials.

15. The neutron capture therapy system according to claim 14, wherein at least one of the beam energy spectrum adjusting members is made of materials capable of generating a neutron beam.

16. The neutron capture therapy system according to claim 9, wherein the cross sections of the beam energy spectrum adjusting member and the neutron generator perpendicular to the irradiation direction of the charged particle beam are circular.

17. A neutron capture therapy system comprising:
an accelerator for generating a charged particle beam;
a neutron generator for generating a neutron beam after being irradiated by the charged particle beam;
a vacuum tube for transporting the charged particles accelerated by the accelerator to the neutron generator;
a beam shaping assembly including a moderator for moderating the neutrons generated by the neutron generator to a preset spectrum and a reflector surrounding the moderator for leading the deflected neutrons back to increase the neutron intensity within the preset spectrum;
a collimator for concentrating the neutrons generated by the neutron generator; and
means for changing the spectrum of the charged particle beam whereby the spectrum of the neutron beam changes.

18. The neutron capture therapy system according to claim 17, wherein a plurality of beam energy spectrum adjusting members are located in the vacuum tube, and move from the first location to the second location separately.

* * * * *